(12) United States Patent
Morella et al.

(10) Patent No.: US 6,197,348 B1
(45) Date of Patent: Mar. 6, 2001

(54) TASTE MASKED LIQUID SUSPENSIONS

(75) Inventors: Angelo Mario Morella, Athelstone; Ian Hamilton Pitman, North Adelaide; Grant Wayne Heinicke, Fairview Park, all of (AU)

(73) Assignee: F H Faulding & Co., Limited, South Australia (AU)

( * ) Notice: Subject to any disclaimer, the term of this patent is extended or adjusted under 35 U.S.C. 154(b) by 0 days.

(21) Appl. No.: 09/180,354

(22) PCT Filed: May 7, 1997

(86) PCT No.: PCT/AU97/00279

§ 371 Date: Feb. 25, 1999

§ 102(e) Date: Feb. 25, 1999

(87) PCT Pub. No.: WO97/41839

PCT Pub. Date: Nov. 13, 1997

(30) Foreign Application Priority Data

May 7, 1996 (AU) .................................................. PN 9697

(51) Int. Cl.[7] ............................... A61K 9/02; A61K 47/32
(52) U.S. Cl. ............................................. 424/497; 514/974
(58) Field of Search ............................... 514/974; 424/497

(56) References Cited

U.S. PATENT DOCUMENTS

| | | | |
|---|---|---|---|
| 5,084,278 | * | 1/1992 | Mehta ................................. 514/974 |
| 5,286,489 | * | 2/1994 | Tsau et al. ........................... 514/974 |
| 5,489,436 | * | 2/1996 | Hoy et al. ............................ 514/974 |
| 5,707,646 | * | 1/1998 | Yajima et al. ....................... 514/974 |

FOREIGN PATENT DOCUMENTS

| | | |
|---|---|---|
| 9119486A | 12/1991 | (WO) . |
| 9425006A | 11/1994 | (WO) . |
| 9505166A | 2/1995 | (WO) . |

* cited by examiner

*Primary Examiner*—Peter F. Kulkosky
(74) *Attorney, Agent, or Firm*—Birch, Stewart, Kolasch & Birch, LLP

(57) ABSTRACT

The present invention relates to a taste-masked pharmaceutical composition. In particular the invention relates to suspensions of microcapsules taste-masked as a function of a polymer coating and the pH of a suspending medium. Surprisingly, a polymer considered permeable maintains taste masking in this media whereas a polymer considered impervious by the industry does not. There is provided a taste masked oral pharmaceutical composition including: a pharmaceutically active ingredient having a pH-dependent solubility; a polymer encapsulating said pharmaceutically active ingredient, said polymer having a quaternary ammonium functionality; a suspending medium for suspending the encapsulated pharmaceutically active ingredient, said medium adjusted to a predetermined pH at which the pharmaceutically active ingredient remains substantially insoluble; and wherein the pharmaceutically active ingredient is taste masked by the combination of the polymer and suspending medium.

16 Claims, 3 Drawing Sheets

TASTE MASKED LIQUID SUSPENSIONS

This application is the national phase under 35 U.S.C. §371 of prior PCT International Application No. PCT/AU97/00279 which has an International filing date of May 7, 1997 which designated th United States of America, the entire contents of which are hereby incorporated by reference.

The present invention relates to a taste-masked pharmaceutical composition. In particular the invention relates to suspensions of microcapsules taste-masked as a function of a polymer coating and the pH of a suspending medium. Surprisingly, a polymer considered permeable maintains tastemasking in this media whereas a polymer considered impervious by the industry does not.

Many drugs are less soluble at higher or lower pH than at the pH value of the mouth, which is around 5.9. Some pharmaceutical compositions have utilised this concept and suspended the drug at a pH in which it remains insoluble. In this condition, the drug can be insufficiently solubilised to be available to taste if the equilibrium concentration is below the taste threshold.

However, problems can arise if all of the suspended particles are not swallowed. If all of the drug particles are not swallowed, the drug which remains in the mouth is able to dissolve at the pH of the mouth which is approximately 5.9. In cases where insolubility is at either end of the pH range, dissolution at a pH of 5.9 could result in a concentration above taste threshold and that the drug becomes available to be tasted.

One means of overcoming the taste problems with delivery of drugs in suspension is the use of polymeric coatings on the drug particles which inhibit or retard the rate of dissolution and solubilisation of the drug. This allows time for all of the particles to be swallowed before the threshold concentration is reached in the mouth and the taste is perceived.

Whilst the use of polymer coats may be effective for retarding dissolution during the time in contact with saliva during the process of swallowing, they have disadvantages in preparing taste-masked liquid formulations intended for long term storage in contact with a liquid medium.

The principal disadvantages are that the drug will equilibrate with the suspension media, and that the coat may weaken, soften, or rupture on prolonged storage.

Japanese Patent No. 80,129,224 provides a method for coating a bitter drug substance with a coating agent containing ethyl cellulose and an antacid. Incorporation of an antacid in the polymer coat on the drug may be unsuitable for maintaining a drug at a predetermined pH (to maintain insolubility) for the reason that when water soluble antacids are used in the coat in a water-based suspension, the antacid would tend to dissolve and leach out, thereby drawing away any means of maintaining a predetermined pH environment and causing instability on the polymer coat. The processes for making such coated drug particles is also difficult since the antacid and polymer have opposite solubilities in the usual coating solvents.

In U.S. Pat. No. 4,656,027 there is provided a method and product wherein a basic substance is mixed with a bitter tasting drug which is insoluble at high pH. The mixture is encapsulated with a polymer which is a cellulose derivative, vinyl derivative or an acid soluble polymer such as a copolymer of dimethylaminomethyl methacrylate. In addition, a method for a mixture of polymer-coated drug with a basic substance is also claimed to give suspensions on reconstitution that give stable taste-masked products.

A major drawback in incorporating the basic substance within the coated drug particle emerges on suspending the particles in aqueous solutions. When suspended in water, the microcapsules absorb water through the pores on the polymer coat, the basic substance dissolves in the absorbed water and exerts a large osmotic pressure that results in either the rupture of the coat or diffusion of the basic substance into the medium. The mixture of basic substance with coated drug particles described in U.S. Pat. No. 4,656,027 is intended as a mixture for reconstitution ie; to be added to water just before use. While this may well serve the purpose, it has been found that the product may not taste-mask as a suspension for a prolonged period.

Australian Patent AU-B-52269/90 describes a method of providing a taste-masked suspension of ibuprofen by maintaining a pH of 1.5–3.5 in a suspension of the drug and providing a buffering capacity within the range of 0.03–0.05 between the initial pH of the formulation and 1.0 pH unit higher.

U.S. Pat. No. 4,788,220 describes a composition for ibuprofen wherein the drug is maintained in suspension with suspending agents and the pH is maintained between 3.5 to 5.

In U.S. Pat. No. 4,788,220 and Australian patent 52269/90 simple suspensions of drug are provided at defined pH ranges. It is now recognised that even if the drug is insolubilised in the formulation by adjustment of the pH, on swallowing a dose, sufficient residue of the drug remains in the oral cavity that after some time when the pH of the mouth equilibrates back to the normal pH of the mouth (average 5.9), the residual drug dissolves rapidly in the mouth leading to a bad taste.

Nowhere in the prior art is it found that a permeable polymer can be applied to drug particles, the polymer coated particles formulated into a suspension, and the resulting suspension remain taste masked for a commercially viable shelf life.

Regarding the pH of the suspension medium the prior art fails to consider several factors that would impact on the long-term physical, chemical and taste stability of the formulation. Whilst the use of an acid or base substance to insolubilise the drug and hence render it unavailable for the taste receptors is a reasonable strategy, an optimum formulation is obtained only when consideration is given to:

(i) the pH of maximum insolubility of the drug;
(ii) the threshold concentration for bitter taste of the drug;
(iii) the minimum buffer strength required in the medium to avoid delayed or after taste;
(iv) the pH limit beyond which further increase or decrease of pH leads to unacceptable instability of the drug; and
(v) the compatibility and chemical, physical and microbial stability of the other ingredients to the pH values of the medium.

Therefore there is a need for a stable taste-masked formulation capable of being maintained in a liquid suspension for a long period of time.

Accordingly, it is an object of the present invention to overcome or at least alleviate one or more of the difficulties related to the prior art.

In a first aspect of the present invention there is provided a taste masked oral pharmaceutical composition including:
   a pharmaceutically active ingredient having a pH-dependent solubility;
   a polymer encapsulating said pharmaceutically active ingredient, said polymer having a quaternary ammonium functionality;

a suspending medium for suspending the encapsulated pharmaceutically active ingredient, said medium adjusted to a predetermined pH at which the pharmaceutically active ingredient remains substantially insoluble; and wherein the pharmaceutically active ingredient is taste masked by the combination of the polymer and suspending medium.

The applicants have found that when microcapsules of a bitter-tasting drug using ethyl cellulose as the polymer coat are formulated in water-based suspensions at a suitable pH, the suspension obtained may be taste-masked for short periods of time but not for longer periods of time, since after a few days the suspension tasted bitter. However, when water permeable cationic methacrylate polymers having a quarternary ammonium functionality such as Eudragit RS100 and Eudragit RL100, were substituted for ethylcellulose as the polymer membrane used in the microencapsulation and formulation of the suspension at the same pH, the resulting suspension remained taste masked for longer.

The pharmaceutically active ingredient may be any one of the class of basic or acidic drugs that dissolve in aqueous systems. As the pH and ionic strength of the medium is selected on the basis of drug stability, solubility and taste threshold, an optimum taste-masking effect that is compatible with the stability of the drug is obtained. The optimum pH is also beneficial in maintaining the stability of the drug, the coating polymer and the coating excipients.

The pharmaceutically active ingredient will be selected for its dependence of solubility on pH. Those drugs which are soluble at a high pH will preferably be maintained in suspension at a low pH where the drug exhibits maximum insolublility. Conversely, those pharmaceuticals which are soluble at a low pH will be preferably maintained in suspension at a high pH where the drug is insoluble. In all cases the polymer membrane avoids solubilisation of residual particles in the mouth and hence provides the taste masking.

The pharmaceutically active ingredient may be any pharmaceutical in the form of its neutral or salt form including the prodrugs and metabolites of the drugs, molecular, acid-base and ion-exchange complexes and may be in the form of crystals, microcapsules or mixtures. The pharmaceutically active ingredient may have a defined particle size distribution, preferably in the region of 0.1–500 $\mu$m, more preferably 1–250 $\mu$m and most preferably 10–150 $\mu$m where there is acceptable mouth feel and little chance of chewing on the residual particles and releasing the drug to taste.

Pharmaceuticals that have high solubility at alkaline pH but are poorly soluble or insoluble at acidic pH are suitable for this application may be selected from the group including non-steroid antiinflammatory drugs such as naproxen, diclofenac sodium, ibuprofen, ketoprofen, valproic acid and indomethacin.

Pharmaceuticals that are poorly soluble or insoluble at alkaline pH but are soluble at acidic pH and suitable for application may be selected from the group including risperidone, roxithromycin, erythromycin and triprolidine.

Preferably the invention further provides a taste-masked oral pharmaceutical composition including:

a pharmaceutical unit including a pharmaceutically active ingredient having a pH-dependent solubility;

a polymer encapsulating said pharmaceutical unit, said polymer having a quaternary ammonium functionally, a suspending medium for suspending the encapsulated pharmaceutically active ingredient, said medium adjusted to a predetermined pH at which the pharmaceutically active ingredient remains substantially insoluble; and wherein the pharmaceutically active ingredient is taste masked by the combination of the polymer membrane and the suspending medium.

The pharmaceutical unit may include along with the pharmaceutically active ingredient other functional components presented for the purpose of modifying the physical, chemical or taste properties of the pharmaceutical. For example the pharmaceutical may be in the form of ion-exchange or cyclodextrin complexes or the pharmaceutical may be included as a mixture or dispersion with various additives such as waxes, lipids, dissolution inhibitors, taste-masking or -suppressing agents, carriers or excipients, and fillers. Suitable fillers may be selected from insoluble materials such as silicon dioxide, titanium dioxide, talc, alumina, starch, kaolin, polacrilin potassium powdered cellulose, and microcrystalline cellulose and mixtures thereof. Soluble fillers may be selected from mannitol, sucrose, lactose, dextrose, sodium chloride, sorbitol and mixtures. The filler may be present in amounts of up to approximately 75% by weight based on the total weight of the unit.

The pharmaceutical unit may be of any suitable particle size. Particle sizes of approximately 0.1 to 500 $\mu$m have been found to be suitable. Particle sizes of approximately 1 to 250 $\mu$m have been found to be particularly suitable. Most preferably 10 to 150 $\mu$m. The pharmaceutical unit may be in the form of a granule, microgranule, powder, pellet, microcapsule, crystal, amorphous solid or precipitate further including the functional components described above.

The polymer used to encapsulate the pharmaceutically active ingredient or the pharmaceutical unit is a polymer having a quaternary ammonium functionality. By this we mean a polymer having quaternary ammonium groups on the polymer backbone such as is provided by the polymers sold under the trade names Eudragit RS100 and Eudragit RL100 or the same polymers in aqueous solution sold under the trade name "Eudragit RS30D" or "Eudragit RL30D". Eudragit RSPO and RLPO may also be used. The applicants have found that these polymers are more effective in preventing the perception of taste of the pharmaceutical when the resulting microcapsules are formulated as suspensions and stored for long periods despite their widely recognised properties of being permeable to water and dissolved drugs. Unlike conventional polymer coatings such as ethyl cellulose known for their properties of providing a dissolution barrier, the quaternary ammonium group polymers have proven to be superior for their taste masking properties when used in combination with pharmaceuticals which are dependent on pH for solubility.

Preferably the polymer is a copolymer of acrylic and methacrylic acid esters with quaternary ammonium groups. More preferably the polymer is a copolymer of methyl methacrylate and triethylammonium methacrylate.

Preferably the polymer is selected from either Eudragit RS or Eudragit RL, available from Rohm. The two polymers may be used individually or in combination to make the polymer coat with corresponding differences in permeability of the coats. Although the pharmaceutically active ingredient is preferably a polymer-coated drug microcapsule, a matrix or mixed particles of polymer and drug may also be obtained by a suitable process for application to this invention. A polymer coat which consists of a blend of the RS or RL polymer along with other pharmaceutically acceptable polymers may also be used for the purposes of the invention. These polymers may be cellulose ethers such as ethyl cellulose, cellulose esters such as cellulose acetate and cellulose propionate, polymers that dissolve at acidic or alkaline pH such as Eudragit E, cellulose acetate phthalate, and hydroxypropylmethyl cellulose phthalate.

The quantity of polymer used in relation to the pharmaceutically active ingredient is in the range of 0.01–10:1, preferably in the range 0.02–1:1, more preferably in the range 0.03–0.5:1 and most preferably in the range of 0.05–0.3:1 byweight.

The pharmaceutically active ingredient or the pharmaceutical unit after encapsulation may be suspended, dispersed or emulsified in the suspending medium.

The suspending medium is preferably a water-based medium, but can be non aqueous carriers as well, constituted at an optimum pH for the pharmaceutically active ingredient or pharmaceutical unit, such that the pharmaceutical remains substantially insoluble. The pH and ionic strength of the medium is preferably selected on the basis of stability, solubility and taste threshold to provide the optimum taste masking effect, and which is compatible with the stability of the drug the polymer coat and the coating excipients.

The optimum pH of insolubility of the drug is determined by conventional solubility determinations at different pH's and ionic strength in the media under consideration.

Buffering agents may be included in the suspending medium for maintaining the desired pH. The buffering agents may include dihydrogen phosphate, hydrogen phosphate, amino acids, citrate, acetate, phthalate, tartrate salts of the alkali or alkaline earth metal cations such as sodium, potassium, magnesium and calcium.

The buffering agents may be used in any suitable combination for achieving the required pH and may be of an buffer strength of 0.01–1 moles/liter of the final formulation, preferably 0.01–0.1 moles/liter, and most preferably 0.02–0.05 moles/liter.

The formulation may further include other dissolved or suspended agents to provide stability to the suspension. These include suspending agents or stabilisers selected from the group including methyl cellulose, sodium aiginate, xanthan gum, (poly)vinyl alcohol, microcrystalline cellulose, colloidal silicas and bentonite clay. Other agents used include preservatives such as methyl, ethyl, propyl and butyl parabens, sweeteners such as sucrose, saccharin sodium, aspartame, mannitol, flavourings such as grape, cherry, peppermint, menthol and vanilla flavours, and antioxidants or other stabilisers.

The resulting pharmaceutical composition, depending on the method employed for production is in the form of a suspension, emulsion, microcapsule including liquid composition or a, hard or soft gelatine capsule, rapid disintegrating tablet, quick melting tablet, effervescent tablet, gel, or liqui-powder which encapsulate the liquid composition for release in the oral cavity. Selection of the solid dose form must be such that the outer shell of the dosage form does not interfere with the suspending medium and the polymer coat encapsulates the pharmaceutically active ingredient.

In the present invention there is provided a method of preparing a taste masked pharmaceutical composition for oral delivery, said composition including
- a pharmaceutically active ingredient having a pH-dependent solubility;
- a polymer encapsulating said pharmaceutically active ingredient, said polymer having a quaternary ammonium functionally;
- a suspending medium for suspending the encapsulated pharmaceutically active ingredient, said medium adjusted to a predetermined pH at which the pharmaceutically active ingredient remains substantially insoluble; and
- wherein the pharmaceutically active ingredient is taste masked by the combination of the polymer and the medium;

which method includes:
providing
- a suitable amount of said pharmaceutically active ingredient;
- a suitable amount of said polymer having a quaternary ammonium functionality;
- a suspending medium adjusted to a pH at which the pharmaceutically active ingredient remains substantially insoluble;

encapsulating said pharmaceutically active ingredient in said polymer; and suspending, dispersing, emulsifying or mixing the encapsulated pharmaceutically active ingredient in the suspending medium.

Preferably the application of this invention includes a preliminary step of determining optimum pH of insolubility of the pharmaceutical by determining solubility at different pH's and ionic strengths. This step is beneficial for determining pH at which to adjust the suspension medium.

In the preferred process of applying this invention, the polymer for encapsulation of the pharmaceutically active ingredient or pharmaceutical unit is dissolved in a solution or solvent chosen for its poor solubility for the pharmaceutically active ingredient and good solubility for the polymer. Examples of appropriate solvents include but are not limited to methanol, ethanol, isopropanol, chloroform, methylene chloride, cyclohexane and toluene, either used in combination or used alone. Aqueous dispersions of polymers may also be used for forming the drug microparticles. Some of the polymer dispersions in water, also known as latexes, are available commercially, for example RS30D, RL30D, NE30-D.

Encapsulation of the pharmaceutically active ingredient or pharmaceutical unit by polymer may be performed by any method such as suspending, dissolving, or dispersing the pharmaceutically active ingredient in a solution or dispersion of polymer coating material and spray drying, fluid-bed coating, simple or complex coacervation, coevaporation, co-grinding, melt dispersion and emulsion-solvent evaporation techniques and so on.

The polymer coated drug powder can also as an alternative be applied for the preparation of reconstitutable powders, ie; dry powder drug products that are reconstituted as suspensions in a liquid vehicle such as water before usage. The reconstitutable powders have a long shelf life and the suspensions, once reconstituted, have adequate taste masking.

The present invention will now be more fully described with reference to the accompanying examples. It should be understood, however that the following description is illustrative only and should not be taken in any way as a restriction on the generality of the invention as specified above.

IN THE FIGURES

EXAMPLE 1

Taste Masked Risperidone

Figure 1:
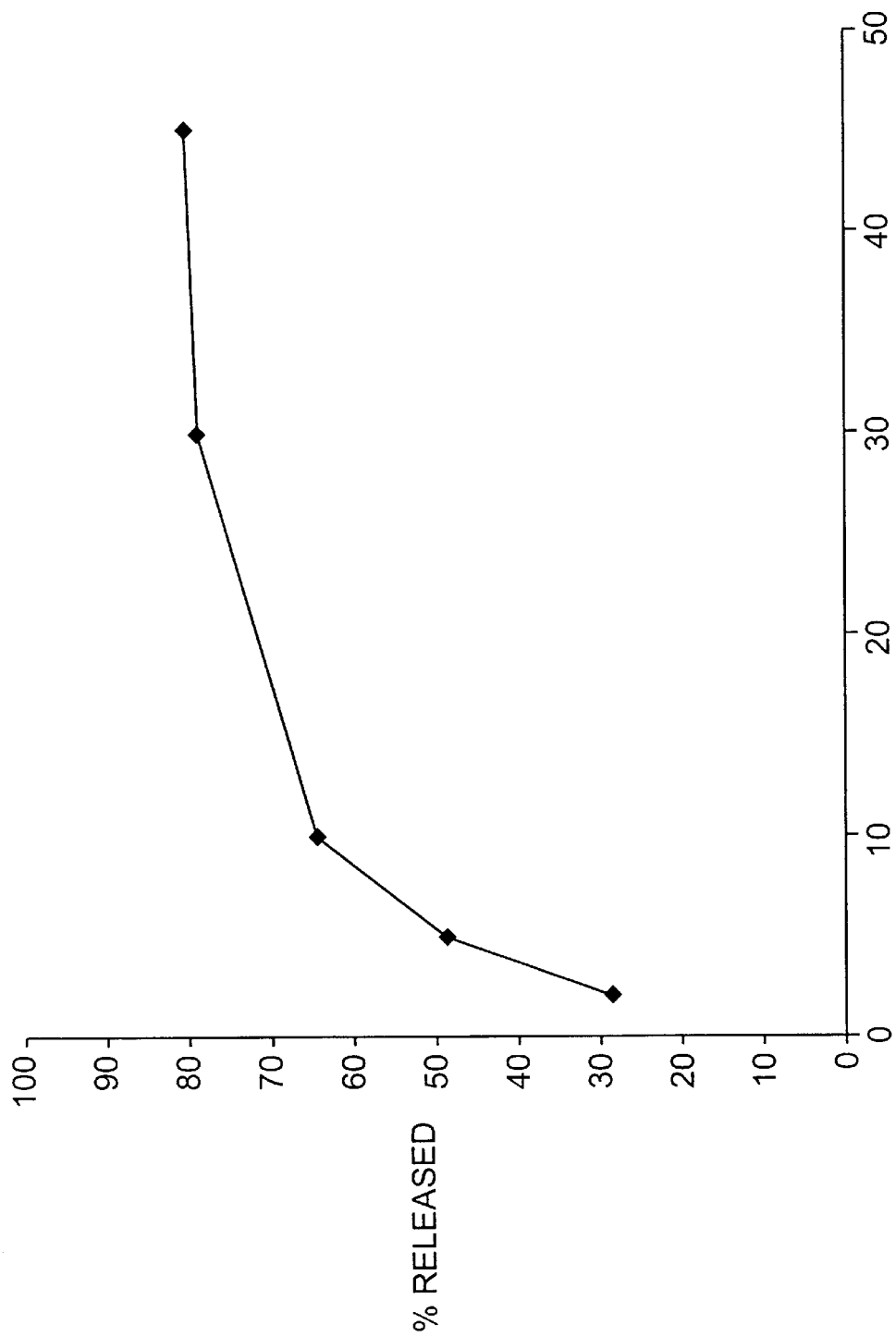
FIG. 1 shows the percentage of Roxithromycin released from coated Powder before suspension.

For a bitter-tasting drug such as Risperidone a pH is selected based on the pH vs solubility profile of the substance. Drug particles of a suitable size are spray-dried from a slurry of the drug in a solution of Eudragit RS to obtain coated particles of the drug. The coated particles which are free-flowing are suspended in a water-based liquid constituted at an optimum pH, and in which suitable functional additives are included to adequately present the product as a final dose form.

20 gms of risperidone of mean particle size of about 20 μm was suspended in a solution of 6.6 gms of Eudragit RS100 in 26.2 gms of isopropyl alcohol. The slurry was continuously atomised into a spray-dryer at an air pressure of 2 bar and inlet temperature of 70° C. The product powder was collected.

A suspension of 1 mg/mL was prepared in buffer at pH 9 with the aid of 2% carboxymethyl cellulose sodium.

A panel of six tasted the suspension weekly over a period of 49 days. The suspension was judged tasteless by all participants at each time point.

EXAMPLE 2

Taste Masked Roxithromycin—I

Roxithromycin (30 grams) was dissolved in a solution of Eudragit RS100 (70 grams) in methylene chloride (560 grams). The solution was pumped through an atomising nozzle into a spray drier with an inlet air temperature of 55° C. The powder was collected and suspended in a 0.05M glycine buffer at pH 10 containing 1% polyvinylpyrollidone. The taste due to the roxithromycin was not detectable 5 days after preparation.

EXAMPLE 3

Taste Masked Roxithromycin—II

Roxithromycin (30 grams) was dissolved in a solution of Eudragit RS100 (70 grams) in methylene chloride (560 grams). Talc (15 grams) was added to the solution. The suspension was pumped through an atomising nozzle into a spray drier and an inlet air temperature of 55° C. The powder was collected and suspended in a 0.05M glycine buffer at pH 10 containing 1% poiyvinylpyrollidone. The suspension had no taste due to roxithromycin on day one or day five after preparation.

EXAMPLE 4

Taste Masked Diclofenac

Diclofenac acid was coated with Eudragit RS-100 by spray drying from methylene chloride under the same conditions as Example 2. The potency of the final powder was 30%. 300 mg of the powder (containing 100 mg of diclofenac) was suspended in a solution containing 500 mg citric acid, 40 ml water and 2 drops of 1% solution of Tween 80 which has a pH of 2.

A comparative solution containing 100 mg of uncoated diclofenac in the same solution was also produced.

The two solutions were then compared by a panel of 5 people.

All taste panellists reported an overwhelming sour taste due to the citric acid after which perceptions due to the drug became apparent. All panellists reported a reduction in the level of bitterness when comparing the suspended coated powder to the suspended uncoated powder. Some panellists reported minor throat bite with the uncoated powder suspensions whereas none was reported with the coated powder.

EXAMPLE 5

Dissolution of Coated Roxithromycin

Roxithromycin was prepared according to Example 2. Dissolution profiles of the Eudragit RS100 coated roxithromycin before and after suspension in a 0.015M glycine buffer at pH10 were compared.

Dissolution tests were conducted using a USP flow through dissolution apparatus at pH 5.8 in 900 ml at 37° C.

Figure 2:
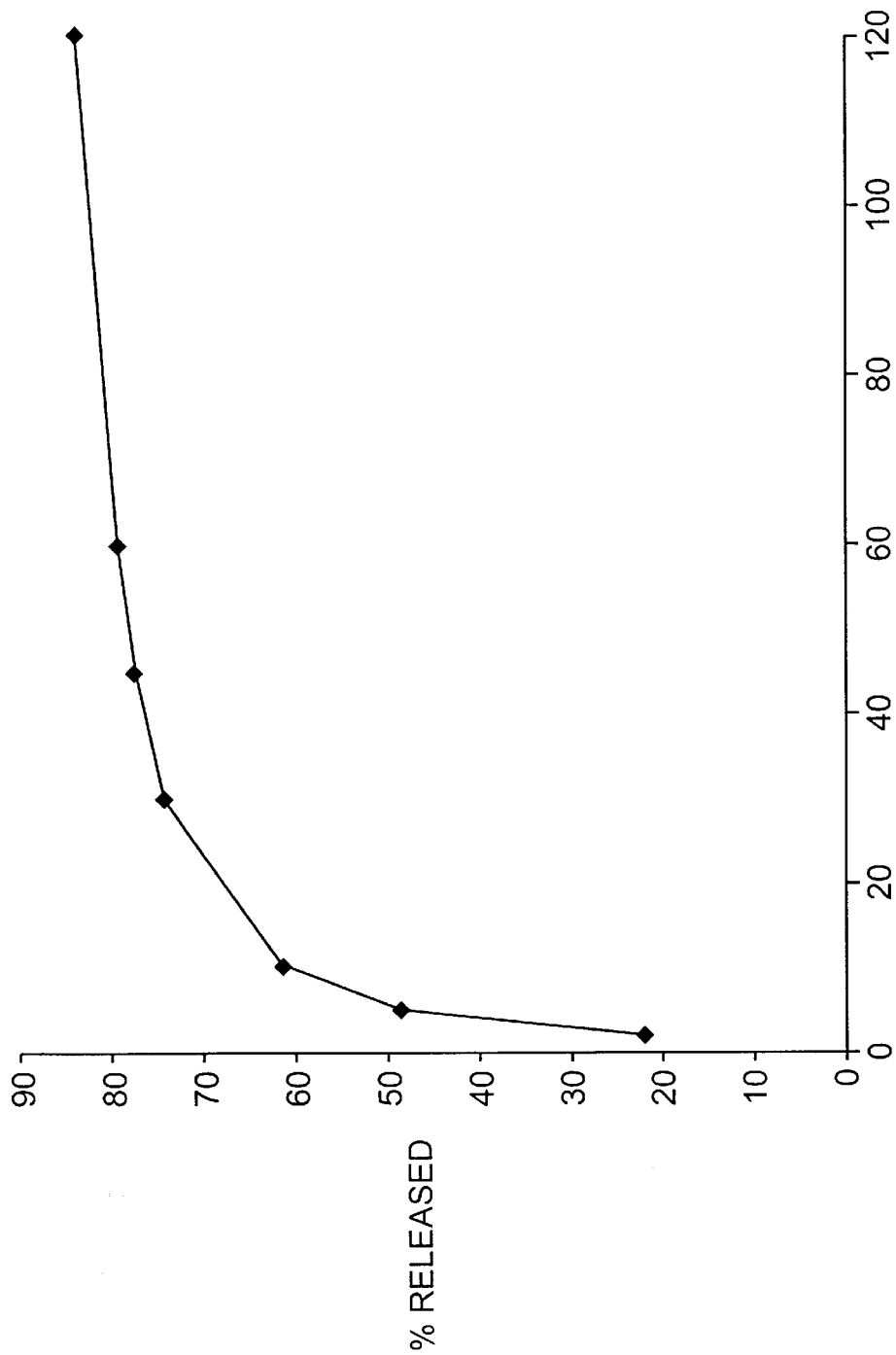
FIG. 2 shows the percentage of Roxithromycin released from coated powder in-vitro after suspension.

Results are shown in FIGS. 1 and 2.

FIG. 1 shows the Percentage of Roxithromycin Released from Coated Powder Before Suspension.

FIG. 2 shows the Percentage of Roxithromycin Released from Coated Powder In-Vitro after Suspension.

The figures illustrate that the release of roxithromycin from the microcapsules is not substantially affected by suspension in a buffered solution.

EXAMPLE 6

Product Analysis Comparison of Roxithromycin and Josamycin

A taste trial was conducted comparing the following suspension products:
1) a suspension containing roxithromycin prepared according to Example 2 on the first day it was made;
2. a suspension containing roxithromycin prepared according to Example 2 on the fifth day after it was made;
3) a commercially available suspension, known as Josacine (®, containing the antibiotic josamycin and available from Rhone Poulenc.

The objectives of the study were to determine if there were any differences in taste and texture
1) between Josamycin and a Roxithromycin formulation (D13218), and
2) between a freshly made and a five-day old Roxithromycin formulation.

The study details and results reported used the Compusense System. This system analyses and evaluates information from a sensory evaluation trial.

Twelve assessors were involved in this study. The study was single blinded, balanced, cross over design.

Figure 3:
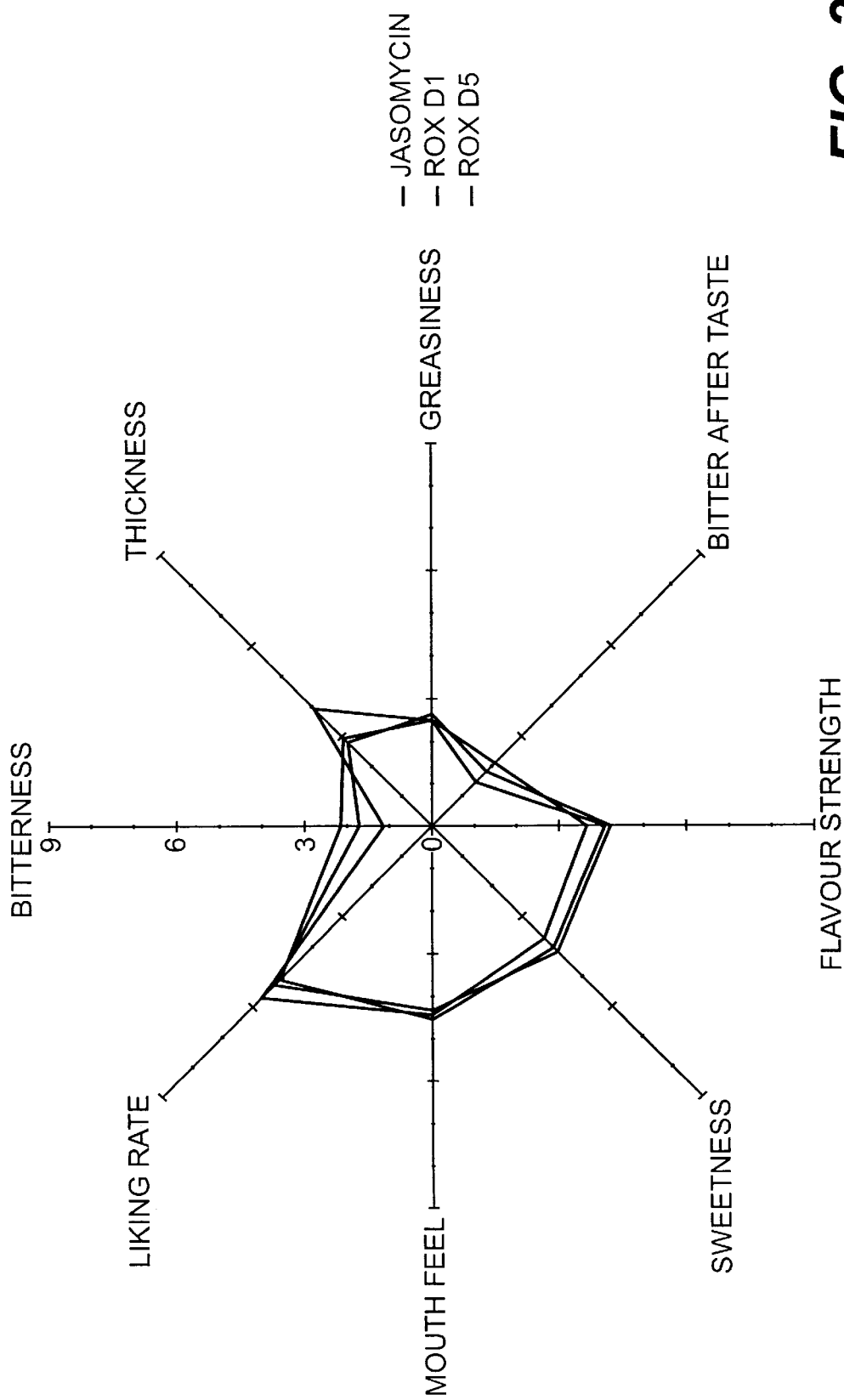
FIG. 3 shows a comparison of after taste, flavour strength, sweetness, mouthfeel, liking rate (how many people liked the taste), bitterness, thickness and greasiness of a roxithromycin suspension after one day and after five days. Compared with a commercially available suspension Josacine®.

The results in FIG. 3 have shown that there were no statistically significant (P>0.05) differences between the reference sample and the development sample, and no statistically significant (P>0.05) difference between the freshly made and the five-day old development samples in the taste attributes tested (i.e. bitterness, sweetness, flavour strength, thickness, greasiness, mouthfeel, bitter after taste and liking rate).

Finally it is to be understood that various other modifications and/or alterations may be made without departing from the spirit of the present invention as outlined herein.

What is claimed is:

1. A taste masked oral pharmaceutical composition in which a pharmaceutically active ingredient is taste masked by a combination of a polymer and a liquid suspending medium, said composition comprising:
   particles of a bitter-tasting pharmaceutically active ingredient having a ph-dependent solubility;
   a polymer encapsulating said particles of pharmaceutically active ingredient, said polymer comprising a member selected from the group consisting of Eudragit RS, Eudragit RL, and mixtures thereof; and
   a liquid suspending medium for suspending the encapsulated pharmaceutically active ingredient, comprising a water-based medium adjusted to a predetermined pH at which the pharmaceutically active ingredient remains substantially insoluble.

2. A taste masked oral pharmaceutical composition according to claim 1 wherein the composition further includes additional polymers selected from the group including cellulose ethers such as ethyl cellulose, cellulose esters such as cellulose acetate and cellulose propionate, polymers that dissolve at acidic or alkaline pH such as Eudragit E, cellulose acetate phthalate, and hydroxypropylmethyl cellulose phthalate.

3. A taste masked oral pharmaceutical composition according to claim 1 wherein a polymer to pharmaceutically active ingredient ratio is in the range of 0.01:1 to 10:1.

4. A taste masked oral pharmaceutical composition according to claim 3 wherein the ratio is in the range of 0.05:1 to 0.3:1.

5. A taste masked oral pharmaceutical composition according to claim 1 wherein said suspending medium further includes a buffering agent selected from the group including dihydrogen phosphate, hydrogen phosphate, amino acids, citrate, acetate, phthalate, tartrate salts of the alkali or alkaline earth metal cations such as sodium, potassium, magnesium and calcium.

6. A taste masked oral pharmaceutical composition according to claim 5 wherein the buffering agent has a buffer strength of 0.1 to 1 mols/liter.

7. A taste masked oral pharmaceutical composition according to claim 6 wherein the buffer strength is 0.02 to 0.05 mols/liter.

8. A taste masked oral pharmaceutical composition according to claim 1 further including a suspending agent or a stabiliser selected from the group including methyl cellulose, sodium alginate, xanthan gum, (poly)vinyl alcohol, microcrystalline cellulose, colloidal silicas, bentonite clay, preservatives selected from the group including methyl, ethyl, propyl and butyl parabens, sweeteners such as sucrose, saccharin sodium, aspartame, mannitol, flavourings such as grape, cherry, peppermint, menthol and vanilla flavours, and antioxidants.

9. A taste masked oral pharmaceutical composition according to claim 1 wherein the pharmaceutically active ingredient is any one of a class of basic or acidic drugs that dissolve in aqueous systems.

10. A taste masked oral pharmaceutical composition according to claim 1 wherein the pharmaceutically active ingredient has a high solubility at alkaline pH and is selected from the group including non-steroid antiinflammatory drugs such as naproxen, diclofenac sodium, ibuprofen, ketoprofen, valproic acid and indomethacin and including the neutral or salt form including the prodrugs and metabolites of the drugs, molecular, acid-base and ion-exchange complexes.

11. A taste masked oral pharmaceutical composition according to claim 1 wherein the pharmaceutically active ingredient has a high solubility at acidic pH and is selected from the group including risperidone, roxithromycin, erythromycin and triprolidine and including the neutral or salt form including the prodrugs and metabolites of the drugs, molecular, acid-base and ion-exchange complexes.

12. A taste masked oral pharmaceutical composition according to claim 1 wherein the pharmaceutically active ingredient has a defined particle size distribution, in the region of 0.1–500 µm.

13. A taste masked oral pharmaceutical composition according to claim 1 including comprising a pharmaceutical unit which includes said pharmaceutically active ingredient having a pH-dependent solubility.

14. A taste masked oral pharmaceutical composition according to claim 13 wherein the pharmaceutical unit further includes waxes, lipids, dissolution inhibitors, taste-masking or -suppressing agents, carriers or excipients, and fillers.

15. A taste masked oral pharmaceutical composition according to claim 13 wherein the pharmaceutical unit has a particle size distribution in the range of 0.1 to 500 µm.

16. A taste-masked oral pharmaceutical composition comprising:
   particles of a bitter-tasting pharmaceutically active ingredient having a pH-dependent solubility;
   a polymer encapsulating said particles of pharmaceutically active ingredient, said polymer comprising a member selected from the group consisting of Eudragit RS and Eudragit RL; and
   a suspending medium for suspending the encapsulated pharmaceutically active ingredient, said medium comprising a water-based medium adjusted by means of a buffering agent to a predetermined pH at which the pharmaceutically active ingredient remains substantially insoluble.

* * * * *